United States Patent
Neergaard (10) Patent No.: US 10,426,726 B2
(45) Date of Patent: Oct. 1, 2019

(54) MEDICAL CHEWING GUM (71) Applicant: FERTIN PHARMA A/S, Vejle (DK)

(72) Inventor: Jesper Neergaard, Aabenraa (DK)

(73) Assignee: FERTIN PHARMA A/S, Vejle (DK)

( * ) Notice: Subject to any disclaimer, the term of this patent is extended or adjusted under 35 U.S.C. 154(b) by 0 days.

(21) Appl. No.: 15/302,441

(22) PCT Filed: Apr. 8, 2015

(86) PCT No.: PCT/DK2015/050084
§ 371 (c)(1),
(2) Date: Oct. 6, 2016

(87) PCT Pub. No.: WO2015/154780
PCT Pub. Date: Oct. 15, 2015

(65) Prior Publication Data
US 2017/0020812 A1 Jan. 26, 2017

(30) Foreign Application Priority Data
Apr. 8, 2014 (DK) .................................. 2014 70183

(51) Int. Cl.
A61K 9/68 (2006.01)
A61K 31/465 (2006.01)
A61K 47/32 (2006.01)
A23G 4/08 (2006.01)
A23G 4/12 (2006.01)
A24B 13/00 (2006.01)
A23G 4/06 (2006.01)

(52) U.S. Cl.
CPC ............ *A61K 9/0058* (2013.01); *A23G 4/068* (2013.01); *A23G 4/08* (2013.01); *A23G 4/12* (2013.01); *A24B 13/00* (2013.01); *A61K 31/465* (2013.01); *A61K 47/32* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,000,321 A | 12/1976 | Mochizuki et al. | |
| 4,737,366 A | 4/1988 | Gergely et al. | |
| 5,017,385 A | 5/1991 | Wienecke | |
| 2001/0002998 A1* | 6/2001 | Ream | A23G 3/343 424/441 |
| 2007/0098845 A1* | 5/2007 | Soper | A23G 4/06 426/5 |
| 2008/0233233 A1 | 9/2008 | Soper et al. | |
| 2008/0241314 A1* | 10/2008 | Hoegl | A23G 4/06 426/6 |
| 2010/0130562 A1* | 5/2010 | Hite | A61K 31/4406 514/343 |
| 2013/0071515 A1* | 3/2013 | Wimmer | A23G 4/08 426/4 |
| 2013/0309352 A1* | 11/2013 | Wimmer | C08L 31/04 426/4 |

FOREIGN PATENT DOCUMENTS

| | | | | |
|---|---|---|---|---|
| CN | 101675105 A | 3/2010 | | |
| EP | 0151344 A2 | 8/1985 | | |
| EP | 0221850 A2 | 5/1987 | | |
| JP | 2005-531317 A | 1/2004 | | |
| JP | 2008-504040 A | 1/2006 | | |
| JP | 2008-515409 A | 4/2006 | | |
| JP | 2009-529317 A | 8/2009 | | |
| JP | 2012-524734 A | 10/2012 | | |
| WO | 2004-004479 A1 | 1/2004 | | |
| WO | 2004004479 A1 | 1/2004 | | |
| WO | WO 2004004479 A1 * | 1/2004 | ............ | A23G 3/004 |
| WO | 2006-000232 A1 | 1/2006 | | |
| WO | 2006000232 A1 | 1/2006 | | |
| WO | WO-2006000232 A1 * | 1/2006 | ............ | A23G 4/068 |
| WO | 2006-037343 A1 | 4/2006 | | |
| WO | 2007-061888 A2 | 5/2007 | | |
| WO | 2008119674 A1 | 10/2009 | | |
| WO | 2010125342 A2 | 4/2010 | | |
| WO | 2010-121619 A1 | 10/2010 | | |
| WO | 2013090653 A1 | 6/2013 | | |

OTHER PUBLICATIONS

Jette Jacobsen, Lana L. Christrupl and Niels-Henrik Jensen. Medicated Chewing Gum. Am J Drug Deliv 2004 2 (2): 75-86. (Year: 2004).*
Patent Cooperation Treaty: International Search Report and Written Opinion for PCT/DK2015/050084; Raposo, Antonio; dated Jun. 25, 2015; 12 pages.
Lene Jorsal, Bo Tandrup, Liisa Vartiainen Lauenborg: "Medicated Chewing Gumdrug Delivery Systems," 2012, pp. 20-22, Retrieved from th einternet: URL:http://www.alkalon.com/sites/default/files/2012.09.25%20Articles%20Medicated%20chewing%20gum%20delivery%20systems.pdf.

* cited by examiner

*Primary Examiner* — Michael P Cohen (57) ABSTRACT

The invention relates to a medical chewing gum comprising gum base polymers and an active pharmaceutical ingredient, the gum base polymers comprising polyvinyl acetate and vinyl laurate-vinyl acetate copolymer in an amount of more than 90% by weight, wherein the gum base polymers include 20-95% by weight of polyvinyl acetate and -80% by weight of vinyl laurate-vinyl acetate copolymer, and wherein the chewing gum contains no polyterpene resins and no resins based on gum rosin, wood rosin or tall oil resin.

21 Claims, 3 Drawing Sheets

MEDICAL CHEWING GUM

CROSS-REFERENCE TO RELATED APPLICATIONS

This application is a U.S. National Phase application submitted under 35 U.S.C. § 371 of Patent Cooperation Treaty application serial no. PCT/DK2015/050084, filed Apr. 8, 2015, and entitled MEDICAL CHEWING GUM, which application claims priority to Danish patent application serial no. PA 2014 70183, filed Apr. 8, 2014, and entitled MEDICAL CHEWING GUM.

Patent Cooperation Treaty application serial no. PCT/DK2015/050084, published as WO2015/0154780, and Danish patent application serial no. PA 2014 70183, are incorporated herein by reference.

TECHNICAL FIELD

The present invention is directed to medical chewing gum. In particular, the present invention relates to medical chewing gum comprising polyvinyl acetate and copolymers of vinyl acetate and vinyl laurate among purely synthetic gum base polymers. The invention is particularly useful for delivery of an active pharmaceutical ingredient, such as nicotine.

BACKGROUND

Pharmaceutical chewing gum is well known for different purposes. Such medical chewing gum may be used for the delivery of an active pharmaceutical ingredient to consumers in need thereof.

Nicotine chewing gum is applied for the purpose of providing a release of nicotine into the saliva in a user's mouth when the user is chewing the nicotine chewing gum. The released nicotine may then be absorbed by the oral mucosa and finally enter the blood stream.

WO 02/102357 A2 discloses a nicotine chewing gum for nicotine delivery by rapid trans-mucosal uptake.

US 2013/0071515 discloses a non-tack gum base comprising polyvinyl acetate and vinyl laurate-vinyl acetate copolymer.

US 2013/0309352 discloses polyvinyl acetate and vinyl laurate-vinyl acetate copolymer as ingredients in a gum base that is simple to process.

One challenge of medical chewing gum in general is that the chewing gum is a complex delivery vehicle. Chewing gum or gum base ingredients may affect multiple properties of the chewing gum. One such example may be that the application of a particular gum base or chewing gum ingredient softens the chewing gum, thereby leading to an increased release due to the eased chewing of the chewing gum. This may be attractive or non-attractive, but a challenge is that the release may be different from the release induced by another ingredient and most of all, the chewing gum texture may simultaneously be affected to a degree that the chewing gum does not have the desired typical textural chewing gum properties. This may e.g. be counteracted by the incorporation of another chewing gum ingredient making the chewing gum harder and/or increasing the elasticity, but this may then affect the desired release and so forth. When referring to typical textural chewing gum properties, it is here noted that the desired rheology of chewing gum is very different from the rheology of typical chewy confectionery such as toffee, chocolate, wine gum, etc. . . . . This is in particular the case in relation to the elastomeric properties required to obtain a confectionery product satisfying the consumer's expectations in relation to a chewing gum.

A particular challenge in relation to nicotine chewing gum is that the nicotine released may cause an unpleasant sensory sensation for the user of the chewing gum which is generally referred to as burning. On the other hand there is a desire to maximize the nicotine release from the chewing gum, as it is this nicotine which provides the user of the chewing gum the desired counteraction of craving.

In other words, the nicotine should be released, but at the same time the nicotine released causes the burning.

It is an object of the present invention to provide medical chewing gum with improved overall properties, such as nicotine chewing gum.

SUMMARY OF THE INVENTION

The invention relates to a medical chewing gum comprising gum base polymers and an active pharmaceutical ingredient, the gum base polymers comprising polyvinyl acetate and vinyl laurate-vinyl acetate copolymer in an amount of more than 90% by weight, wherein the gum base polymers include 20-95% by weight of polyvinyl acetate and 5-80% by weight of vinyl laurate-vinyl acetate copolymer, and wherein the chewing gum contains no polyterpene resins and no resins based on gum rosin, wood rosin or tall oil resin.

According to an embodiment of the invention, it is possible to omit polyterpene resins, resins based on gum rosin, wood rosin or tall oil resin in the chewing gum or gum base formulation. It is thereby possible to obtain a reproducible medical chewing gum without affecting the release of pharmaceutical ingredient substantially. It is therefore possible to apply chewing gums and gum bases for medical purposes without significantly changing the properties of the chewing gum or gum base when natural resins are omitted.

According to an advantageous embodiment of the invention an attractive texture may be obtained by the application of synthetic gum base polymers while retaining an acceptable release of active ingredients. It should in particular be noted that the application of synthetic gum base polymers without any application of polyterpene resins or resins based on gum rosin, wood rosin or tall oil resin provides an attractive base for an active pharmaceutical ingredient and a related buffer.

According to an advantageous embodiment of the invention, the medical chewing gum comprises gum base polymers and an active pharmaceutical ingredient, the gum base polymers consisting of synthetic gum base polymers, and the gum base polymers comprising polyvinyl acetate and vinyl laurate-vinyl acetate copolymer in an amount of more than 90% by weight, wherein the gum base polymers include 20-95% by weight of polyvinyl acetate and 5-80% by weight of vinyl laurate-vinyl acetate copolymer, and wherein the chewing gum contains no polyterpene resins and no resins based on gum rosin, wood rosin or tall oil resin.

According to an embodiment of the invention, it is possible to omit polyterpene resins, resins based on gum rosin, wood rosin or tall oil resin in the chewing gum or gum base formulation. It is thereby possible to obtain a reproducible medical chewing gum without affecting the release of pharmaceutical ingredient substantially. It is therefore possible to apply chewing gums and gum bases for medical purposes without significantly changing the properties of the chewing gum or gum base formulation when natural resins are omitted.

According to an advantageous embodiment of the invention an attractive texture may be obtained by the application of synthetic gum base polymers while retaining an acceptable release of active ingredients. It should in particular be noted that the application of synthetic gum base polymers without any application of polyterpene resins or resins based on gum rosin, wood rosin or tall oil resin provides an attractive base for an active pharmaceutical ingredient and a related buffer.

According to an advantageous embodiment of the invention, the medical chewing gum comprises gum base polymers, an active pharmaceutical ingredient and buffer, the gum base polymers comprising polyvinyl acetate and vinyl laurate-vinyl acetate copolymer in an amount of more than 90% by weight, wherein the gum base polymers include 20-95% by weight of polyvinyl acetate and 5-80% by weight of vinyl laurate-vinyl acetate copolymer, and wherein the chewing gum contains no polyterpene resins and no resins based on gum rosin, wood rosin or tall oil resin.

According to an embodiment of the invention, it is possible to omit polyterpene resins, resins based on gum rosin, wood rosin or tall oil resin in the chewing gum or gum base formulation. It is thereby possible to obtain a reproducible medical chewing gum without affecting the release of the release of pharmaceutical ingredient substantially. It is therefore possible to apply chewing gums and gum bases for medical purposes without significantly changing the properties of the chewing gum or gum base formulation when natural resins are omitted.

According to an advantageous embodiment of the invention an attractive texture may be obtained by the application of synthetic gum base polymers while retaining an acceptable release of active ingredients. It should in particular be noted that the application of synthetic gum base polymers without any application of polyterpene resins or resins based on gum rosin, wood rosin or tall oil resin provides an attractive base for an active pharmaceutical ingredient and a related buffer.

According to an advantageous embodiment of the invention, the medical chewing gum comprises gum base polymers, an active pharmaceutical ingredient and buffer, the gum base polymers consisting of synthetic gum base polymers, and the gum base polymers comprising polyvinyl acetate and vinyl laurate-vinyl acetate copolymer in an amount of more than 90% by weight, wherein the gum base polymers include 20-95% by weight of polyvinyl acetate and 5-80% by weight of vinyl laurate-vinyl acetate copolymer, and wherein the chewing gum contains no polyterpene resins and no resins based on gum rosin, wood rosin or tall oil resin.

According to an embodiment of the invention, it is possible to omit polyterpene resins, resins based on gum rosin, wood rosin or tall oil resin in the chewing gum or gum base formulation. It is thereby possible to obtain a reproducible medical chewing gum without affecting the release of the release of pharmaceutical ingredient substantially. It is therefore possible to apply chewing gums and gum bases for medical purposes without significantly changing the properties of the chewing gum or gum base formulation when natural resins are omitted.

According to an advantageous embodiment of the invention an attractive texture may be obtained by the application of synthetic gum base polymers while retaining an acceptable release of active ingredients. It should in particular be noted that the application of synthetic gum base polymers without any application of polyterpene resins or resins based on gum rosin, wood rosin or tall oil resin provides an attractive base for an active pharmaceutical ingredient and a related buffer.

In an embodiment of the invention, the active pharmaceutical ingredient is nicotine.

According to the provisions of the invention it is possible to obtain a chewing gum which may even release more nicotine than conventional nicotine chewing gums and without causing an increase of the so-called burning sensation.

It is even more noted that the burning sensation may be comparable to conventional nicotine chewing gum even when conventional chewing gum release significantly slower than the inventive chewing gum.

According to a further embodiment of the invention, the provided chewing gum or chewing gum base may be less susceptible to degradation of the nicotine and thereby form an attractive carrier of nicotine while possessing both advantageous release properties and desired textural properties with respect to e.g. elasticity.

In an embodiment of the invention nicotine is present in an amount of 0.5-8 mg, preferably 1-5 mg, such as 2 mg or 4 mg.

A single piece of chewing gum may typically contain 0.5-8 mg of nicotine, preferably 1-5 mg, such as 2 mg or 4 mg.

A buffer of a chewing gum in the present context is characterized by maintaining the pH level within certain relatively constant pH values. In the present context, the buffer must be matched to the active pharmaceutical ingredient contained in the chewing gum, such as nicotine.

The buffer may to some extent be microencapsulated or otherwise coated as granules with polymers and/or lipids being less soluble in saliva than is the one or more buffering agents. Such microencapsulation controls the dissolution rate thereby extending the time frame of the buffering effect. In order to increase the buffering capacity, one may e.g. add further buffering agents to the chewing gum.

In an embodiment of the invention, the medical chewing gum exhibits several very advantageous properties such as improved texture, improved release, improved robustness and improved stability of an active pharmaceutical ingredient, such as nicotine.

Improved texture according to an embodiment of the invention may be obtained through sufficient elastic properties of the applied gum base polymer blend to resemble a chewing gum feel.

The improved release according to an embodiment of the invention may be obtained through the fact that the synthetic gum base polymers are able to release both the hydrophilic buffer and the nicotine in a synchronous way, still facilitating a relatively high degree of taste masking by means of sweeteners and flavors.

The improved robustness according to an embodiment of the invention may be obtained through the fact that synthetic polymers applied in combination offers the robustness to buffers and flavors usually obtained through mandatory use of natural resins.

Improved stability according to an embodiment of the invention may be obtained by means of no addition of polyterpene resins and no addition of resins based on gum rosin, wood rosin or tall oil rosin.

Furthermore, the medical chewing gum of the invention may exhibit less variation with respect to release of an active pharmaceutical ingredient, such as nicotine, when compared to conventional nicotine chewing gum.

In an embodiment of the invention, nicotine is selected from the group consisting of a nicotine salt, the free base form of nicotine, a nicotine derivative, such as a nicotine cation exchanger, such as nicotine polacrilex resin, a nicotine inclusion complex or nicotine in any non-covalent binding; nicotine bound to zeolites; nicotine bound to cellulose, such as microcrystalline, or starch microspheres, and mixtures thereof.

In an embodiment of the invention, the nicotine salts are selected from the group comprising nicotine hydrochloride, nicotine dihydrochloride, nicotine monotartrate, nicotine bitartrate, nicotine sulfate, nicotine zinc chloride, nicotine salicylate, or any combination thereof.

In an embodiment of the invention, nicotine is present as a nicotine polacrilex resin.

In an embodiment of the invention, nicotine is added to the chewing gum as tobacco powder.

In an embodiment of the invention, at least a part of the nicotine is contained in tobacco powder.

In an embodiment of the invention the nicotine is selected from the group consisting of a nicotine salt, the free base form of nicotine, a nicotine derivative, such as a nicotine cation exchanger, such as nicotine polacrilex resin, a nicotine inclusion complex or nicotine in any non-covalent binding; nicotine bound to zeolites; nicotine bound to cellulose, such as microcrystalline, or starch microspheres, and mixtures thereof.

It is generally noted that specific examples and explanation specifically referring to nicotine as an active pharmaceutical ingredient against craving in no way restricts the scope of the invention with respect to use of other tobacco alkaloids for the same specific purpose. A specific mentioning of nicotine at any place in this application is only used for the purpose of exemplifying the invention in a tangible way and not for the purpose of excluding alternative functionally equivalents.

It should generally be noted that nicotine is a preferred tobacco alkaloid.

In the present invention, the term nicotine encompasses nicotine or a nicotine derivative in any form such as, e.g. physical forms like amorphous, crystalline, polymerphous etc. or chemical form like isomers and enantiomers etc. as well as any pharmaceutically acceptable salts, complex or solvate thereof. Nicotine may be selected from nicotine base, nicotine hydrochloride, nicotine dihydrochloride, nicotine monotartrate, nicotine bitartrate, nicotine sulfate, nicotine zinc chloride such as zinc chloride monohydrate and nicotine salicylate.

In an embodiment of the invention the nicotine salts are selected from the group comprising nicotine hydrochloride, nicotine dihydrochloride, nicotine monotartrate, nicotine bitartrate, nicotine sulfate, nicotine zinc chloride, nicotine salicylate, or any combination thereof.

In an embodiment of the invention, the weight ratio between polyvinyl acetate and vinyl laurate-vinyl acetate copolymer is from 8:1 to 2:3.

In an embodiment of the invention, the weight ratio between polyvinyl acetate and vinyl laurate-vinyl acetate copolymer is from 5:1 to 2:3.

In an embodiment of the invention, the weight ratio between polyvinyl acetate and vinyl laurate-vinyl acetate copolymer is from 3:2 to 2:3.

In an embodiment of the invention the weight ratio between vinyl acetate monomers of vinyl laurate-vinyl acetate copolymer and vinyl laurate monomers of vinyl laurate-vinyl acetate copolymer is less than 90:10, such as 80:20, such as 60:40.

In an embodiment of the invention, the weight-average molecular weight Mw of polyvinyl acetate is from 5,000 to 120,000, such as 5,000 to 70,000, such as 7,000 to 25,000, and the weight-average molecular weight Mw of vinyl acetate-vinyl laurate copolymer is from 80,000 to 700,000, such as 100,000 to 600,000, such as 120,000 to 250,000.

In an embodiment of the invention the chewing gum comprises a plasticizer.

In an embodiment of the invention the chewing gum comprises wax.

In an embodiment of the invention the chewing gum comprises fat.

In an embodiment of the invention the chewing gum comprises an emulsifier.

In an embodiment of the invention the chewing gum comprises one or more fillers.

In an embodiment of the invention the synthetic gum base polymers are forming part of a gum base.

In an embodiment of the invention the gum base comprises 15-45% by weight of polyvinyl acetate, 10-30% by weight of vinyl laurate-vinyl acetate copolymers, 15-45% by weight of fillers, 5-30% by weight of waxes or fats, 1-10% by weight of plasticizers and 1-10% by weight of emulsifiers.

In an embodiment of the invention the gum base comprises 20-35% by weight of polyvinyl acetate, 12-25% by weight of vinyl laurate-vinyl acetate copolymer, 20-30% by weight of fillers, 10-20% by weight of waxes or fats, 2-8% by weight of plasticizers and 2-8% by weight of emulsifiers.

In an embodiment of the invention, the chewing comprises buffer in the amount of ½ to 5% by weight of the chewing gum, such as 1 to 4%, such as 2 to 5%, such as 3 to 5%, such as 3 to 4%, such as 1 to 3%.

In an embodiment of the invention, the chewing gum comprises a water insoluble gum base and a water soluble bulk portion, wherein the gum base and the bulk portion are mixed to form a final chewing gum core, and wherein the gum base is buffered before mixing with the bulk portion, and the buffered gum base comprises from 2 to 20% by weight of the gum base before mixing with the bulk portion, such as 2 to 10%, such as 3 to 8%, such as 4 to 8%, such as 5 to 8%, such as 2 to 15%, such as 4 to 15%, such as 4 to 12%.

In an embodiment of the invention, the buffer is selected from the group consisting of a carbonate, including bicarbonate or sesquicarbonate, glycerinate, phosphate, glycerophosphate, acetate, glyconate or citrate of an alkali metal, such as potassium or sodium, e.g. trisodium and tripotassium citrate, or ammonium, tris buffer, amino acids, and mixtures thereof.

In an embodiment of the invention, the buffer comprises sodium carbonate, sodium bicarbonate or any combination thereof.

The buffer may to some extent be microencapsulated or otherwise coated as granules with polymers and/or lipids being less soluble in saliva than is the one or more buffering agents. Such microencapsulation controls the dissolution rate whereby the time frame of the buffering effect is extended.

In an embodiment of the invention, the chewing gum comprises a water insoluble gum base and a water soluble bulk portion, wherein the gum base and the bulk portion is mixed to form a final chewing gum core, and wherein the gum base is buffered before mixing with the bulk portion, and the buffered gum base comprises buffer from 2 to 20% by weight of the gum base before mixing with the bulk portion, such as 2 to 10%, such as 3 to 8%, such as 4 to 8%, such as 5 to 8%, such as 2 to 15%, such as 4 to 15%, such as 4 to 12%.

In an embodiment of the invention, the buffer comprises sodium carbonate, sodium bicarbonate or potassium carbonate.

According to a preferred embodiment of the invention, the buffer comprises sodium carbonate. The use of this buffer together with the stated polyvinyl acetate and vinyl laurate-vinyl acetate copolymer facilitates and advantageous release of buffer matching the released nicotine, while at the same time obtaining a robust chewing gum which is not dissolved by the buffer.

In an embodiment of the invention, the gum base polymers further comprises one or more elastomers selected from the group consisting of styrene-butadiene copolymers (SBR), polyisobutylene isobutylene-isoprene copolymers (IIR or butyl rubber), polyethylene or any combination thereof.

The use of a supplemental elastomers selected from the group consisting of styrene-butadiene copolymers (SBR), polyisobutylene (PIB), isobutylene-isoprene copolymers (IIR or butyl rubber), polyethylene or any combination thereof has proven unexpectedly advantageous in the sense that the synthetic elastomers may assist in obtaining a less pronounced burning sensation while maintaining a high level of nicotine release.

According to an advantageous embodiment of the invention, the gum base polymers further comprises one or more elastomers in an amount of 0.1-10% by weight, such as in an amount of 1-8% by weight, such as in an amount of 1.5-6% by weight.

According to an advantageous embodiment of the invention, the weight-average molecular weight Mw of polyisobutylene (PIB) ranges from 37,000 to 1,000,000, such as 37,000 to 110,000, such as 37,000 to 70,000.

In an embodiment of the invention, the chewing gum comprises emulsifiers in an amount in the range of 0.1% to 25% by weight of said chewing gum.

In an embodiment of the invention, the emulsifiers are selected from the group of cyclodextrins, polyoxyethylene castor oil derivatives, polyoxyethylene alkyl ethers, macrogol alkyl ethers, block copolymers of ethylene and propylene oxides, polyoxyethylene alkyl ethers, polyoxyethylene glycols, polyoxyethylene sorbitan fatty acid esters, polyoxyethylene (20) sorbitan monostearates, polyoxyethylene (20) sorbitan monooleates, polyoxyethylene stearates, sobitan esters, diacetyl tartaric ester of monoglycerides, lactylated monoglycerides, or any combination thereof.

The preferred emulsifiers are selected from the group of acetylated monoglycerides, mono- and/or di-glycerides of fatty acids such as glycerol monostearate, acetem, lecithines and any combination thereof.

In an embodiment of the invention the chewing gum comprises one or more fillers including magnesium- and calcium carbonate, sodium sulphate, ground limestone, silicate compounds such as magnesium- and aluminum silicate, kaolin and clay, aluminum oxide, silicium oxide, talc, titanium oxide, mono-, di- and tri-calcium phosphates, cellulose polymers, such as wood, starch polymers, fibres and combinations thereof.

A preferred filler is calcium carbonate, talc, cellulose polymers or combinations thereof.

In an embodiment of the invention, the filler is present in an amount of 5-45% by weight of the chewing gum, such as in an amount of 10-40% by weight of the chewing gum.

In an embodiment of the invention, the chewing gum comprises one or more plasticizers in an amount in the range of 0.1% to 25% by weight of said chewing gum.

In an embodiment of the invention the plasticizer comprises diacetin and/or triacetin.

In an embodiment of the invention the plasticizers comprise glycerol and/or medium chain triglycerides.

A preferred plasticizer is triacetin.

A further suitable plasticizer is miglyol.

In an embodiment of the invention, the chewing gum comprises wax selected from the group consisting of paraffin waxes, microcrystalline waxes, polyethylene waxes and natural waxes.

In an embodiment of the invention the chewing gum comprises fat selected from the group consisting of animal fats and vegetable fats.

Waxes and fats are used for the adjustment of the texture and for softening of the chewing gum base when preparing chewing gum bases. In connection with the present invention, any conventionally used and suitable type of natural and synthetic wax and fat may be used, such as for instance rice bran wax, polyethylene wax, petroleum wax (refined paraffin and microcrystalline wax), sorbitan monostearate, tallow, propylene glycol, paraffin, beeswax, carnauba wax, candelilla wax, cocoa butter, degreased cocoa powder and any suitable oil or fat, as e.g. completely or partially hydrogenated vegetable oils or completely or partially hydrogenated animal fats.

In an embodiment of the invention, the chewing gum comprises flavor in an amount between 0.01 and 10% by weight of the chewing gum such as in an amount between 0.01 and 5% by weight of the chewing gum.

Non-exhaustive examples of flavors suitable in embodiments of the present invention are coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits mentioned above.

In an embodiment of the invention the chewing gum comprises high intensity sweetener.

Preferred high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside and the like, alone or in combination.

In an embodiment of the invention, the chewing gum comprises bulk sweeteners including sugar and/or sugarless components.

In an embodiment of the invention, the chewing gum comprises bulk sweetener in the amount of 5 to about 95% by weight of the chewing gum, more typically constitute 20 to about 80% by weight, and more commonly, 30 to 60% by weight of the gum.

The sweeteners often fill the role of bulking agents in the gum. The sweeteners are improving juiciness of the gum and are supporting the flavor profile of the gum.

Sugar sweeteners generally include, but are not limited to saccharide-containing components commonly known in the chewing gum art, such as sucrose, dextrose, maltose, saccharose, lactose, sorbose, dextrin, trehalose, D-tagatose, dried invert sugar, fructose, levulose, galactose, corn syrup solids, glucose syrup, hydrogenated glucose syrup, and the like, alone or in combination.

The sweetener can be used in combination with sugarless sweeteners.

Generally, sugarless sweeteners include components with sweetening characteristics but which are devoid of the commonly known sugars and comprise, but are not limited to, sugar alcohols such as sorbitol, mannitol, xylitol, hydrogenated starch hydrolyzates, maltitol, isomalt, erythritol, lactitol and the like, alone or in combination.

In an embodiment of the invention, the synthetic gum base polymers are resins and elastomers.

In an embodiment of the invention, the synthetic gum base polymers are forming part of the gum base.

In an embodiment of the invention the medical chewing gum is free of antioxidants.

The amount of antioxidants in medical chewing gum according to embodiments of the invention may be reduced or antioxidants may even be avoided. This may be due to improved stability of the chewing gum with respect to oxidation.

In an embodiment of the invention the chewing gum comprises gum base in an amount of 30-75% by weight of the chewing gum before any optionally applied coating, such as 35-70% by weight of the chewing gum or 40-65% by weight of the chewing gum or 45-60% by weight of the chewing gum.

In an embodiment of the invention the chewing gum is manufactured in a two step process, the first step including the process of providing the gum base in a first mixing process and a further step including the process of mixing the gum base with further chewing gum components in a further mixing process.

In an embodiment of the invention the chewing gum is manufactured in a one step process by means of an extruder.

According to an advantageous embodiment of the invention, the medical chewing gum has a tan (delta) of less than 1.2, such as less than 1.1, such as less than 1.0.

According to an advantageous embodiment of the invention, the medical chewing gum has a tan delta of less than 1.2, such as less than 1.1, such as less than 1.0 wherein said tan (delta) is measured at an oscillation frequency of frequency of approximately 1 Hz.

According to an advantageous embodiment of the invention, the medical chewing gum has a tan delta of less than 1.2, such as less than 1.1, such as less than 1.0 wherein said tan (delta) is measured at an oscillation frequency of frequency of approximately 1 Hz and wherein said tan delta is measured at an oscillation torque of about 8 to 12 µN·m.

According to an advantageous embodiment of the invention, the medical chewing gum has a tan delta of at less than 1.2, such as less than 1.1, such as less than 1.0 wherein said tan (delta) is measured at an oscillation frequency of frequency of approximately 1 Hz and wherein said tan delta is measured at an oscillation torque of about 8 to 12 µN·m and wherein said tan delta is measured by AR 1000 rheometer from TA Instruments and at a temperature of 37° C.

According to an advantageous embodiment of the invention, the medical chewing gum has a tan delta of less than 1.2, such as less than 1.1, such as less than 1.0 wherein said tan (delta) is measured at an oscillation frequency of frequency of approximately 1 Hz and wherein said tan delta is measured at an oscillation torque which provides a linear viscoelastic response (LVR).

According to an advantageous embodiment of the invention, the medical chewing gum has a tan delta of at less than 1.2, such as less than 1.1, such as less than 1.0 wherein said tan (delta) is measured at an oscillation frequency of frequency of approximately 1 Hz and wherein said tan delta is measured at an oscillation torque which provides a linear viscoelastic response (LVR) and wherein said tan delta is measured by AR 1000 rheometer from TA Instruments and at a temperature of 37° C.

According to an advantageous embodiment of the invention, the tan (delta) is defined as (loss modulus G"/storage modulus G').

The invention relates in a further aspect to a chewing gum comprising gum base polymers and an active pharmaceutical ingredient, the gum base polymers comprising polyvinyl acetate and vinyl laurate-vinyl acetate copolymer in an amount of more than 90% by weight, wherein the gum base polymers include 20-95% by weight of polyvinyl acetate and 5-80% by weight of vinyl laurate-vinyl acetate copolymer, and wherein the chewing gum contains no polyterpene resins and no resins based on gum rosin, wood rosin or tall oil resin.

According to an advantageous embodiment of the invention, the chewing gum according to the above aspect may be according to any of claims.

The invention relates in a further aspect to a chewing gum comprising gum base polymers and an active pharmaceutical ingredient, the gum base polymers comprising polyvinyl acetate and vinyl laurate-vinyl acetate copolymer in an amount of more than 90% by weight, wherein the gum base polymers include 20-95% by weight of polyvinyl acetate and 5-80% by weight of vinyl laurate-vinyl acetate copolymer, and wherein the chewing gum base contains no polyterpene resins and no resins based on gum rosin, wood rosin or tall oil resin.

According to an advantageous embodiment of the invention, the chewing gum according to the above aspect may be according to any of claims.

According to an embodiment of the invention it is possible to obtain a chewing gum with improved reproducibility.

BRIEF DESCRIPTION OF THE DRAWINGS

The invention will be described in the following with reference to the figures in which.

DETAILED DESCRIPTION

Definitions

As used herein, by the phrase "chewing gum" is meant any chewing gum such as extruded chewing gum, centre-filled chewing gum, toffee-imitating chewing gum, or compressed chewing gum, slabs or sticks.

By the terms "gum base" and "gum base matrix" is meant the mainly water-insoluble and hydrophobic gum base ingredients that are mixed together, typically before the bulk portion of the chewing gum is added. The "gum base" may contain gum base polymers and plasticizers, waxes, emulsifiers, fats and/or fillers. The gum base may thus designate the typical water-insoluble chewing gum components, which may be manufactured in a first step and subsequently mixed with the mainly water soluble portion in a second step. The term gum base may, evidently, also refer to the relevant gum base components fed into an extruder and forming part of the final chewing gum when mixed with the chewing gum components in the extruder.

The term "bulk portion" intends to mean the mainly water-soluble and hydrophilic chewing gum ingredients that may be mixed into the gum base matrix, either in a separate process or in a one-step process by means of an extruder.

The term "gum base polymer" intends to mean resins and elastomers and does not include, for example, plasticizers, waxes, emulsifiers, fats or fillers although these may also be present in a gum base.

The term "weight of the chewing gum" or similar wording meaning the same is defined in the present context as weight of the chewing gum, not including the weight of an outer coating, such as a hard coating, soft coating, and the like.

By the phrase "texture" is meant a qualitative measure of the visco-elastic properties of the chewing gum and of the overall mouth-feel experienced by the user during the chewing process. Thus the term "texture" encompasses measurable quantities such as hardness and elasticity as well as more subjective parameters related to the chew-feel experienced by a user.

The term "natural resin", as used herein, means resinous compounds being either polyterpenes derived from terpenes of natural origin or resinous compounds derived from gum rosin, wood rosin or tall-oil rosin.

The term "synthetic polymer", as used herein, means polymers industrially synthesized by appropriate polymerization techniques.

The term "buffer", as used herein, refers to pH-control agents.

Description

According to the invention, buffer is added, to the medical chewing gum.

Suitable buffers may be selected from the group consisting of tris buffers, amino acid buffers, carbonate, including bicarbonate or sesquicarbonate, glycerinate, phosphate, glycerophosphate, acetate, glyconate or citrate of an alkali metal, such as potassium and sodium, e.g. trisodium and tripotassium citrate, or ammonium, and mixtures thereof.

Buffer may be present in an amount of 0.5-10% by weight of the chewing gum.

A preferred buffer is sodium carbonate or a mixture of sodium carbonate and sodium bicarbonate.

Further suitable buffers may be selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Magnesium carbonate, Magnesium oxide, or any combination thereof.

The buffer may to some extent be microencapsulated or otherwise coated as granules with polymers and/or lipids being less soluble in saliva. Such microencapsulation controls the dissolution rate whereby the time frame of the buffering effect is extended.

However, in presently preferred embodiments an alkaline buffer is preferred, such as sodium carbonate and/or sodium hydrogen carbonate.

According to embodiments of the invention a preferred amount of gum base matrix in the final chewing gum is 30-75% by weight of the chewing gum before any optionally applied coating, such as 35-70% by weight of the chewing gum or 40-65% by weight of the chewing gum or 45-60% by weight of the chewing gum.

The formulation of gum bases can vary depending on the particular product to be prepared and on the desired masticatory and other sensory characteristics of the final product.

Besides the polyvinyl acetate and the vinyl laurate-vinyl acetate copolymer, the gum base may optionally contain further synthetic elastomers in an amount of less than 10% by weight of the gum base polymers such as less than 8% by weight of the gum base polymers or less than about 5% by weight of the gum base polymers.

Such synthetic elastomers may be selected from the group consisting of styrene-butadiene copolymers (SBR), polyisobutylene, isobutylene-isoprene copolymers (butyl rubber, BR), polyurethane and polyethylene.

Preferred synthetic elastomers are styrene-butadiene copolymers (SBR), polyisobutylene and isobutylene-isoprene copolymers (BR).

If non-tack chewing gum is desired, copolymers of methyl vinyl ether and maleic acid and derivatives therof, such as Gantrez and/or copolymers of polyisoprene-graft maleic anhydride (PIP-g-MA) with polyethylene-glycol (PEG) or methoxy-polyethylene-glycol (MPEG) side chains, such as REV-7 provided by Revolymer, may be among the gum base polymers.

The gum base matrix may further comprise:

0 to 40% by weight waxes, 5 to 35% by weight softeners other than waxes, such as plasticizers, fats and emulsifiers, 0 to 50% by weight filler, and 0 to 5% by weight of miscellaneous ingredients such as antioxidants, colorants, etc.

Natural resins are not used according to the invention. According to the invention the medical chewing gum is free of natural rosin esters, often referred to as ester gums including as examples glycerol esters of partially hydrogenated rosins, glycerol esters of polymerised rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins, synthetic resins such as terpene resins derived from alpha-pinene, beta-pinene, and/or d-limonene, and natural terpene resins.

In an embodiment of the invention, the medical chewing gum comprises further chewing gum ingredients selected from the group consisting of flavors, dry-binders, tableting aids, anti-caking agents, emulsifiers, antioxidants, enhancers, absorption enhancers, high intensity sweeteners, softeners, colors, active ingredients, water-soluble indigestible polysaccharides, water-insoluble polysaccharides or any combination thereof.

According to embodiments of the invention, said emulsifiers are selected from the group of cyclodextrins, polyoxyethylene castor oil derivatives, polyoxyethylene alkyl ethers, macrogol alkyl ethers, block copolymers of ethylene and propylene oxides, polyoxyethylene alkyl ethers, polyoxyethylene glycols, polyoxyethylene sorbitan fatty acid esters, polyoxyethylene (20) sorbitan monostearates, polyoxyethylene (20) sorbitan monooleates, polyoxyethylene stearates, sobitan esters, diacetyl tartaric ester of monoglycerides, lactylated monoglycerides, mono- and/or di-glycerides of fatty acids such as glycerol monostearate, Acetem, lecithines or any combination thereof.

In an embodiment of the invention, said chewing gum comprises emulsifiers in an amount in the range of 0.1% to 25% by weight of said chewing gum.

In an embodiment of the invention the chewing gum comprises flavor. Flavor may typically be present in amounts between 0.01 and 10% by weight of the chewing gum, such as between 0.01 and 5% by weight of the chewing gum.

Non-exhaustive examples of flavors suitable in embodiments of the present invention are coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits mentioned above.

Petroleum waxes aid in the curing of the finished gum made from the gum base as well as improve shelf life and texture. Wax crystal size influences the release of flavor. Those waxes high in iso-alkanes have a smaller crystal size than those waxes high in normal-alkanes, especially those with normal-alkanes of carbon numbers less than 30. The smaller crystal size allows slower release of flavor since there is more hindrance of the flavor's escape from this wax versus a wax having larger crystal sizes.

Petroleum wax (refined paraffin and microcrystalline wax) and paraffin wax are composed of mainly straight-chained normal-alkanes and branched iso-alkanes. The ratio of normal-alkanes to iso-alkanes varies.

The normal-alkanic waxes typically have carbon chain lengths >C-18 but the lengths are not predominantly longer than C-30. The branched and ring structures are located near the end of the chain for those waxes that are predominantly normal-alkanic. The viscosity of normal-alkanic waxes is <10 mm2/s (at 100° C.) and the combined number average molecular weight is <600 g/mole.

The iso-alkanic waxes typically have carbon lengths that are predominantly greater than C-30. The branched chains and ring structures are located randomly along the carbon chain in those waxes that are predominantly iso-alkanic. The viscosity of iso-alkanic waxes is greater than 10 mm2/s (at 100° C.) and the combined number average molecular weight is >600 g/mole.

Synthetic waxes are produced by means that are atypical for petroleum wax production and are thus not considered petroleum wax. The synthetic waxes may include waxes containing branched alkanes and copolymerized with monomers such as, but not limited to propylene, polyethylene, and Fischer Tropsch type waxes. Polyethylene wax is a synthetic wax containing alkane units of varying lengths having attached thereto ethylene monomers.

Waxes and fats are conventionally used for the adjustment of the texture and for softening of the chewing gum base when preparing chewing gum bases. In connection with the present invention, any conventionally used and suitable type of natural and synthetic wax and fat may be used, such as for instance rice bran wax, polyethylene wax, petroleum wax (refined paraffin and microcrystalline wax), sorbitan monostearate, tallow, propylene glycol, paraffin, beeswax, carnauba wax, candelilla wax, cocoa butter, degreased cocoa powder and any suitable oil or fat, as e.g. completely or partially hydrogenated vegetable oils or completely or partially hydrogenated animal fats.

Suitable vegetable oils include but are not limited to oils that are based on coconut, palm, palm kernel, cotton seed, rape seed or sunflower and combinations thereof.

Antioxidants prolong shelf life and storage of gum base, finished gum or their respective components including fats and flavor oils.

Antioxidants suitable for use in gum base include butylated hydroxyanisole (BHA), butylated hydroxytoluene (BHT), betacarotenes, tocopherols, acidulants such as Vitamin C, propyl gallate, other synthetic and natural types or mixtures thereof.

In some embodiments, one or more colors can be included in the chewing gum.

According to the invention the chewing gum comprises nicotine. The nicotine is in a form selected from nicotine salts, nicotine free base, nicotine bound in a complex, or any combination thereof.

In an embodiment of the invention, the complex comprises an ion exchange resin.

In an embodiment of the invention, said ion exchange resin is a weakly acidic cation exchange resin.

According to an embodiment of the invention, a preferred example of a weakly acidic cation exchange resin is polacrilex.

In an embodiment of the invention, said complex comprises an adsorbent.

In an embodiment of the invention, said adsorbent is selected from the group consisting of finely divided silicic acid, amorphous silica, magnesium silicate, calcium silicate, kaolin, clays, crystalline aluminosilicates, macaloid bentonite, activated carbon, alumina, hydroxylapatite, microcrystalline cellulose, or any combination thereof.

In an embodiment of the invention, said nicotine salts are selected from the group comprising nicotine hydrochloride, nicotine dihydrochloride, nicotine monotartrate, nicotine bitartrate, nicotine sulfate, nicotine zinc chloride, nicotine salicylate, or any combination thereof.

According to further embodiments of the invention, the medical chewing gum, may comprise an active pharmaceutical ingredient selected from the group consisting of antihistamines, anti-smoking agents, agents used for diabetes, decongestrants, peptides, pain-relieving agents, antacids, nausea-relieving agents, statines, or any combination thereof.

In an embodiment of the invention, the active pharmaceutical ingredients are selected from the group consisting of cetirizine, levo cetirizine, nicotine, nicotine polacrilex, nicotine in combination with alkaline agents, metformin, metformin HCL, phenylephrine, GLP-1, exenatide, MC-4 receptor antagonist, PPY(3-36), deca-peptide, KSL-W (acetate), fluor, chlorhexidine, or any combination thereof.

In an embodiment of the invention, the active pharmaceutical ingredients are selected from the group consisting of:

loratadine, des-loratadine, nicotine bitartrate, nicotine in combination with caffeine, nicotine antagonists, combinations thereof or compounds comprising one or more of these, pseudoephedrine, flurbiprofen, paracetamol, acetylsalicylic acid, Ibuprofen, antacida, cimetidine, ranitidine, ondansetron, granisetron, metoclopramid, simvastatin, lovastatin, fluvastatin, acyclovir, benzydamin, rimonabant, varenicline, sildenafil, naltrexone, fluor in combination with fruit acids, derivatives, salts or isomers of chlorhexidine, or any combination thereof.

In an embodiment of the invention, the active pharmaceutical ingredient is selected from the therapeutical groups consisting of:

Antipyretic, Anti allergic, Anti-arrytmic, Appetite suppressant, Anti-inflammatory, Broncho dilator, Cardiovascular drugs, Coronary dilator, Cerebral dilator, Peripheral vasodilator, Anti-infective, Psychotropic, Anti-manic, Stimulant, Decongestant, Gastro-intestinal sedative, Sexual dysfunction agent, Desinfectants, Anti-anginal substance, Vasodilator, Anti-hypertensive agent, Vasoconstrictor, Migraine treating agent, Anti-biotic, Tranquilizer, Anti-psychotic, Anti-tumor drug, Anticoagulant, Hypnotic, Sedative, Anti-emetic, Anti-nauseant, Anti-convulsant, Neuromuscular agent, Hyper and hypoglycaemic, Thyroid and anti-thyroid, Diuretic, Anti-spasmodic, Uterine relaxant, Anorectics, Spasmolytics, Anabolic agent, Erythropoietic agent, Anti-asthmatic, Expectorant, Cough suppressant, Mucolytic, Anti-uricemic agent, Dental vehicle, Breath freshener, Antacid, Anti-diuretic, Anti-flatulent, Betablocker, Teeth Whitener, Enzyme, Co-enzyme, Protein, Energy Booster, Fiber, Probiotics, Prebiotics, Antimicrobial agent, NSAID, Anti-tussives, Decongestrants, Anti-histamines, Anti-diarrheals, Hydrogen antagonists, Proton pump inhibitors, General nonselective CNS depressants, General nonselective CNS stimulants, Selectively CNS function modifying drugs, Antiparkinsonism, Narcotic-analgetics, Analgetic-antipyretics, Psychopharmacological drugs, diagnostica sex hormones allergens, antifungal agents, Chronic Obstructive Pulmonary Disease (COPD) or any combination thereof.

In an embodiment of the invention, the active pharmaceutical ingredient is selected from the group consisting of: ace-inhibitors, antianginal drugs, antiarrhythrmas, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, antimanics, anti-nauseants, anti-stroke agents, anti-thyroid preparations, anti-tumor drugs, anti-viral agents, acne drugs, alkaloids, amino acid preparations, anti-tussives, antiuricemic drugs, anti-viral drugs, anabolic preparations, systemic and non-systemic antiinfective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies such as sildenafil citrate, which is currently marketed as Viagra™, fertility agents, gastrointestinal agents, homeopathic remedies, hormones, hypercalcemia and hypocalcemia management agents, immunomodulators, inmosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids such as bromocryptine or nicotine, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

In an embodiment of the invention, the active pharmaceutical ingredient is selected from the group consisting of anti-histamines, decongestants, smoking cessation aids, diabetes II agents, or any combination thereof.

In an embodiment of the invention, the active pharmaceutical ingredient is selected from the group consisting of ephedrine, pseudo ephedrine, caffeine, loratadine, sildenafil, simvastatin, sumatriptan, acetaminophen, calcium carbonate, vitamin D, ibuprofen, aspirin, alginic acid in combination with aluminum hydroxide and sodium bicarbonate, ondansetron, Tibolon, Rimonabant, Varenicline, allergenes, sitagliptin or any derivatives thereof, salts thereof, isomers thereof, combinations thereof or compounds comprising one or more of these.

According to embodiments of the invention, the chewing gum comprises active ingredients.

In an embodiment of the invention, the active ingredient is selected from the group consisting of phytochemicals, such as resveratrol and anthocyanin; herbals, such as green tea or thyme; antioxidants, such as polyphenols; micronutrients; mouth moisteners, such as acids; throat soothing ingredients; appetite suppressors; breath fresheners, such as zinc compounds or copper compounds; diet supplements; cold suppressors; cough suppressors; vitamins, such as vitamin A, vitamin C or vitamin E; minerals, such as chromium; metal ions; alkaline materials, such as carbonates; salts; herbals, dental care agents, such as re-mineralization agents, antibacterial agents, anti-caries agents, plaque acid buffering agents, tooth whiteners, stain removers or desensitizing agents; and combinations thereof.

In an embodiment of the invention, said active ingredient is selected from the group consisting of di-peptides, tri-peptides, oligo-peptides, deca-peptides, deca-peptide KSL, deca-peptide KSL-W, amino acids, proteins, or any combination thereof.

In an embodiment of the invention, said active ingredient comprise probiotic bacteria, such as lactobacilli, bifidobacteria, lactococcus, streptococcus, leuconostoccus, pediococcus or enterococcus.

In an embodiment of the invention, said active ingredient is selected from the group consisting of nutraceuticals, nutrients, nutritional supplements, dental care agents, herbals, and the like and combinations thereof.

High intensity artificial sweetening agents can also be used according to preferred embodiments of the invention. Preferred high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside and the like, alone or in combination.

In order to provide longer lasting sweetness and flavor perception, it may be desirable to encapsulate or otherwise control the release of at least a portion of the artificial sweeteners.

Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another chewing gum component such as a resinous compound.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated sweetener will be proportionately higher. Combinations of sugar and/or non-sugar sweeteners may be used in the chewing gum.

A chewing gum and/or gum base may, if desired, include one or more fillers/texturizers including as examples, magnesium- and calcium carbonate, sodium sulphate, ground limestone, silicate compounds such as magnesium- and aluminum silicate, kaolin and clay, aluminum oxide, silicium oxide, talc, titanium oxide, mono-, di- and tri-calcium phosphates, cellulose polymers, such as wood, and combinations thereof.

According to an embodiment of the invention, one preferred filler/texturizer is calcium carbonate.

A number of chewing gum components well known within the art may be applied within the scope of the present invention. Such components comprise but are not limited to waxes, fats, softeners, fillers, bulk sweeteners, flavors, antioxidants, emulsifiers, colouring agents, binding agents and acidulants.

In an embodiment of the invention, the chewing gum is provided with an outer coating selected from the group consisting of hard coating, soft coating and edible film-coating or any combination thereof.

The following non-limiting examples illustrate different variations of the present invention. The examples are meant for indicating the inventive concept; hence the mentioned examples should not be understood as exhaustive for the present invention.

In case of example VIII, GB 108, comparative example IX, GB 109, and standard gumbase example XX, GB 110, which include butyl rubber (BR), BR is added in the initial mixing step, and the mixing time is extended to a total of about 90-105 minutes.

In case of comparative example IX, GB 109, the natural resin is added before the addition of triacetin, and in case of standard example XX, GB 110, the natural resin is added after about 30 minutes before the addition of softeners.

The gum base compositions were as displayed in table 1 here below, the amounts given corresponding to percentages by weight:

TABLE 1

Gum base compositions, VA-VL I = vinyl acetate-vinyl laurate copolymer (Vinnapas B 500/40VL, supplied by Wacker); VA-VL II = vinyl acetate-vinyl laurate copolymer (Vinnapas B 500/20VL, supplied by Wacker);

| Raw material | Ex. I | Ex. II | Ex. III | Ex. IV | Ex. V | Ex. VI | Ex. VII | Ex. VIII | Ex. IX comp. | Ex. X Std |
|---|---|---|---|---|---|---|---|---|---|---|
| GB no. | 101 | 102 | 103 | 104 | 105 | 106 | 107 | 108 | 109 | 110 |
| VA-VL I | 20 |  | 14 |  | 22 | 21 | 20 | 20 | 10 |  |
| VA-VL II |  | 20 |  | 22 |  |  |  |  |  |  |
| PVA I | 32 | 33 | 18 | 35 | 33 | 31 | 30 | 30 | 20 | 25 |
| PVA II |  |  | 5.0 |  |  |  |  |  |  |  |
| PIB |  |  |  |  |  | 3.0 | 5.0 | 3.0 | 3.0 | 5 |
| BR |  |  |  |  |  |  |  | 2.0 | 2.0 | 5 |
| Nat. resin |  |  |  |  |  |  |  |  | 20 | 25 |
| Calcium Carbonate |  | 19 |  | 22 | 17 | 17 | 17 | 17 | 17 | 17 |
| Talc | 20 |  | 41 |  |  |  |  |  |  |  |
| Triacetin | 8 | 8 | 6 | 7 | 2 | 2 | 2 | 2 | 2 |  |
| Emulsifier | 5 | 7 | 3 | 8 | 9 | 9 | 9 | 9 | 9 | 5 |
| Wax, microcrystalline | 13 | 13 | 10 |  | 12 | 12 | 12 | 12 | 12 | 13 |
| Veg. fat | 2 |  | 3 | 6 | 5 | 5 | 5 | 5 | 5 | 5 |
| Total | 100 | 100 | 100 | 100 | 100 | 100 | 100 | 100 | 100 | 100 |

PVA II = polyvinyl acetate (Vinnapas B 30 sp, supplied by Wacker);
PVA II = polyvinyl acetate (Vinnapas B 30 sp, supplied by Wacker);
PIB = polyisobutylene (Oppanol B12, supplied by BASF);
BR = butyl rubber (isobutylene-isoprene copolymer);
Nat. resin = glycerol ester of hydrogenated gum rosin.

EXAMPLES

Example 1

Composition of Gum Bases

Ten different gum bases (GB), given GB nos. 101-110, were prepared by the following process:

The polymers PVA, VA-VL, and optionally PIB are mixed at 120° C. together with filler, here calcium carbonate or talc, in a mixing kettle having horizontally placed Z-shaped arms for mixing.

When the polymers are softened, triacetin is added, followed by addition of emulsifier, wax and vegetable fat.

After a total mixing time of about 45-60 minutes, the mixture is discharged into a pan and allowed to cool to room temperature.

Example 2

Composition Nicotine Chewing Gum

Nicotine chewing gum (NCG), given CHG nos.1001-1010, using gum bases nos. 101-110 from Table 1, respectively, were prepared as follows:

Gum base and filler are mixed in a mixing kettle having horizontally placed Z-shaped arms for mixing. The kettle was preheated to a temperature of up to approximately 50° C.

When the content of the kettle is homogeneous, the other ingredients are added according to a specified time schedule. Nicotine is added during the first half of the mixing process and may be added as pure nicotine, as a nicotine salt or bound to an ion exchange resin, for example Amberlite IRP 64.

The chewing gum compositions were as displayed in table 2 here below, the amounts given corresponding to percentages by weight:

TABLE 2

Nicotine chewing gum compositions.

| Raw material | Ex. XI | Ex. XII | Ex. XIII | Ex. XIV | Ex. XV | Ex. XVI | Ex. XVII | Ex. XVIII | Ex. XIX Comp. | Ex. XX Std |
|---|---|---|---|---|---|---|---|---|---|---|
| NCG no. | 1001 | 1002 | 1003 | 1004 | 1005 | 1006 | 1007 | 1008 | 1009 | 1010 |
| GB 101 | 52 | | | | | | | | | |
| GB 102 | | 52 | | | | | | | | |
| GB 103 | | | 52 | | | | | | | |
| GB 104 | | | | 52 | | | | | | |
| GB 105 | | | | | 52 | | | | | |
| GB 106 | | | | | | 52 | | | | |
| GB 107 | | | | | | | 52 | | | |
| GB 108 | | | | | | | | 52 | | |
| GB 109 | | | | | | | | | 52 | |
| GB 110 | | | | | | | | | | 52 |
| Filler | 20 | 20 | 20 | 20 | 20 | 20 | 20 | 20 | 20 | 20 |
| Nicotine | 0.2 | 0.2 | 0.2 | 0.2 | 0.2 | 0.2 | 0.2 | 0.2 | 0.2 | 0.2 |
| Ion exchange resin | 0.8 | 0.8 | 0.8 | 0.8 | 0.8 | 0.8 | 0.8 | 0.8 | 0.8 | 0.8 |
| Sodium hydrogen carbonate | 1.0 | 1.0 | 1.0 | 1.0 | 1.0 | 1.0 | 1.0 | 1.0 | 1.0 | 1.0 |
| Sodium carbonate | 2.0 | 2.0 | 2.0 | 2.0 | 2.0 | 2.0 | 2.0 | 2.0 | 2.0 | 2.0 |
| Sorbitol powder | 18 | 18 | 18 | 18 | 18 | 18 | 18 | 18 | 18 | 18 |
| Liquid sweetener | 1.5 | 1.5 | 1.5 | 1.5 | 1.5 | 1.5 | 1.5 | 1.5 | 1.5 | 1.5 |
| Intense sweetener | 0.4 | 0.4 | 0.4 | 0.4 | 0.4 | 0.4 | 0.4 | 0.4 | 0.4 | 0.4 |
| Flavor | 4.1 | 4.1 | 4.1 | 4.1 | 4.1 | 4.1 | 4.1 | 4.1 | 4.1 | 4.1 |
| Total | 100 | 100 | 100 | 100 | 100 | 100 | 100 | 100 | 100 | 100 |

Example 3

Evaluation of Release from Chewing Gums XI, XII, XIV, XV and XIX of Example 2

The below table 3 illustrates API release (release of nicotine in the present example) of the chewing gums XI, XII, XIV, XV and XIX of example 2 (corresponding to gum bases I, II, IV, V and IX of example 1).

The release of the API in this example is determined in vitro. The measurements were carried out according to the procedure set forth in the Ph. Eur. 6$^{th}$ ed. 2.9.25, in a phosphate buffer with pH=7.4, a chewing rate of 60 chew per minute, and with the temperature of the medium set at 37° C.

One piece of chewing gum was chewed at specified time intervals 0, 5, 10, 20 and 30 minutes. Then, the API content of the samples before and after chewing was analyzed according to standard HPLC-techniques.

It is noted that the chewing gums XI, XII and XV resemble the release of comparative example XIX even though natural resin has been completely omitted. This is contrary to the expectations due to the fact that natural resins are typically regarded necessary for counteracting a fast release of chewing gum ingredients such as API, flavours and sweeteners.

TABLE 3

Nicotine release in percentage of actual content of nicotine contained in the chewing gum.

| Chewing gum according to example | % RELEASE at minutes | | | |
|---|---|---|---|---|
| | 5 min | 10 min | 20 min | 30 min |
| Ex. XI | 47 | 68 | 84 | 90 |
| Ex. XII | 47 | 70 | 85 | 91 |
| Ex. XIV | 46 | 73 | 87 | 92 |
| Ex. XV | 38 | 67 | 85 | 90 |
| Ex. XIX Comparative | 46 | 70 | 82 | 88 |

Figure 1:
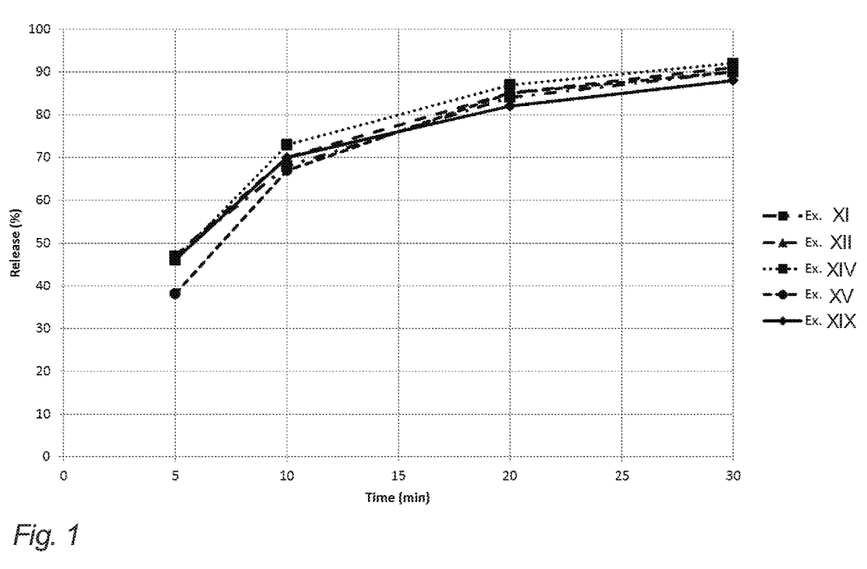
FIG. 1 illustrates the release of API according to an example.

The abovementioned release is also illustrated in FIG. 1, clearly showing that the release of the natural resin-containing comparative example and the natural resin-free inventive examples is comparable.

Example 4

Evaluation of Texture of Chewing Gums XI, XII, XIV, XV and XIX of Example 2

The below table 4 illustrates the texture evaluation of the chewing gums XI, XII, XIV, XV, and XIX of example 2 (corresponding to gum bases I, II, IV, V and IX of example 1).

A test panel of 4 persons trained for sensory evaluation was used. The trained persons chewed the samples at a rate of 60 chews per minute and for each sample evaluated each of the sensory attributes Initial chew softness, Softness after 5 minutes and Elasticity after 5 minutes on a 5 point scale.

For Initial softness and Softness after 5 minutes a score of 5 denotes the highest softness and 1 the least softness (most hardness). For Elasticity a score of 5 denotes the highest elasticity (ie. the most elastic, bouncy chew) and 1 the lowest elasticity (ie. the most plastic chew).

TABLE 4

Texture evaluation of softness and elasticity as tested by a sensory panel

| Chewing gum according to example | Initial chew softness | Softness after 5 minutes | Elasticity after 5 minutes |
|---|---|---|---|
| XI | 4 | 4 | 3 |
| XII | 3 | 4 | 3 |
| XIV | 2 | 3 | 2 |
| XV | 1 | 1 | 3 |
| XIX (comparative) | 4 | 4 | 4 |

The evaluation above confirms that the inventive samples XI, XII XIV and XV provides a texture resembling that of conventional chewing gum.

It is furthermore noted that chewing gums XI and XII closely resembles the texture of the comparative chewing gum XIX.

Example 5

Evaluation of Burning Onset of Nicotine Chewing Gums XV, XVI, XVII, XVIII, and XIX of Example 2

Onset of burning was evaluated by a test panel of 5 trained persons. The trained persons chewed the samples at a rate of 60 chews per minute and for each sample registered onset of the burning sensation.

The below table 5 illustrates the burning onset of the chewing gums XV, XVI, XVII, XVIII, and XIX of example 2 (corresponding to gum bases V, VI, VII, VIII, and IX of example 1) and a chewing gum XX based on a standard gum base comprising natural resin, elastomer and no vinyl acetate-vinyl laurate copolymer.

TABLE 5

Evaluation of burning onset as tested by a sensory panel

| Chewing gum according to example | Burning onset in seconds |
|---|---|
| XV | 45 |
| XVI | 50 |
| XVII | 55 |
| XVIII | 60 |
| XIX (comparative) | 60 |
| Std. XX | 55 |

As illustrated by the above table 5, inventive chewing gums free of natural resin may be obtained having characteristics with regard to burning onset which are comparable to natural resin-containing chewing gums and standard gum base chewing gums.

It is furthermore noted that chewing gums XVI to XVIII are indeed very close to the burning of the conventional chewing gum XX (std) and the comparative chewing gum XIX in spite of the fact that the corresponding release is different.

Example 6

Evaluation of Nicotine Release from Nicotine Chewing Gums XV, XVI, XVIII, and XIX of Example 2

The below table 6 illustrates API release (release of nicotine in the present example) of the chewing gums XV, XVI, XVIII, and XIX of example 2 (corresponding to gum bases V, VI, VIII, and IX of example 1) and a chewing gum based on a standard gum base comprising natural resin, elastomer and no vinyl acetate-vinyl laurate copolymer.

The release of the API in this example is determined in vitro. The measurements were carried out according to the procedure set forth in the Ph. Eur. $6^{th}$ ed. 2.9.25, in a phosphate buffer with pH=7.4, a chewing rate of 60 chew per minute, and with the temperature of the medium set at 37° C.

One piece of chewing gum was chewed at specified time intervals 0, 5, 10, 20 and 30 minutes. Then, the API content of the samples before and after chewing was analyzed according to standard HPLC-techniques.

It is noted that the chewing gums XV, XVI, and XVIII resemble the release of comparative example XIX even though the natural resin has been completely omitted. This is contrary to the expectations due to the fact that natural resins are typically regarded necessary for counteracting a fast release of chewing gum ingredients such as API, flavours and sweeteners.

TABLE 6

Nicotine release in percentage of actual content of nicotine contained in the chewing gum.

| Chewing gum according to example | % RELEASE at minutes | | | |
|---|---|---|---|---|
| | 5 min | 10 min | 20 min | 30 min |
| Ex. XV | 38 | 67 | 85 | 90 |
| Ex. XVI | 36 | 66 | 85 | 91 |
| Ex. XVIII | 38 | 68 | 87 | 92 |
| Ex. XIX (comparative) | 46 | 70 | 82 | 88 |
| Std. XX | 12 | 33 | 60 | 75 |

Figure 2:
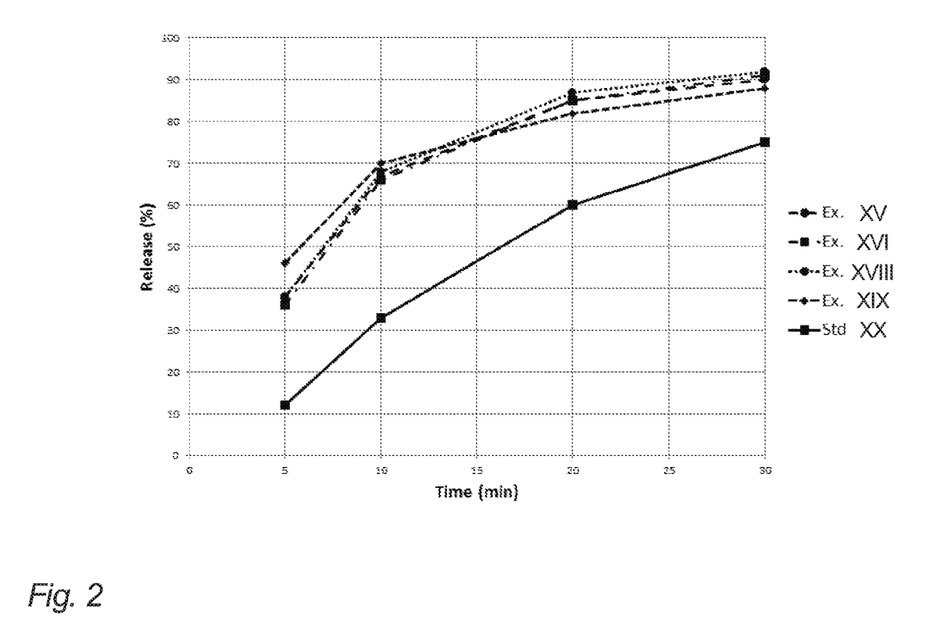
FIG. 2 illustrates the release of nicotine according to an example.

The abovementioned release is also illustrated in FIG. 2, clearly showing that the release of the natural resin-containing example and the natural resin-free examples are comparable.

Example 7

Evaluation of Texture of Nicotine Chewing Gums XV, XVI, XVII, XVIII, and XIX of Example 2

The below table 7 illustrates the texture of the chewing gums XV, XVI, XVII, XVIII, and XIX of example 2 (corresponding to gum bases V, VI, VII, VIII, and IX of example 1) and a chewing gum XX based on a standard gum base X.

A test panel of 4 persons trained for sensory evaluation was used. The trained persons chewed the samples at a rate of 60 chews per minute and for each sample evaluated each of the sensory attributes Initial chew softness, Softness after 5 minutes and Elasticity after 5 minutes on a 5 point scale.

For Initial softness and Softness after 5 minutes a score of 5 denotes the highest softness and 1 the least softness (most hardness). For Elasticity a score of 5 denotes the highest elasticity (ie. the most elastic, bouncy chew) and 1 the lowest elasticity (ie. the most plastic chew).

TABLE 7

Texture evaluation of softness and elasticity as tested by a sensory panel

| Chewing gum according to example | First chew softness | Softness after 5 minutes | Elasticity after 5 minutes |
|---|---|---|---|
| XV | 1 | 1 | 3 |
| XVI | 1-2 | 1-2 | 3-4 |
| XVII | 2-3 | 3 | 4 |
| XVIII | 2 | 2 | 4 |
| XIX (comparative) | 4 | 4 | 4 |
| Std. XX | 4 | 4 | 3 |

The evaluation above confirms that the inventive samples XI to XIX provide a texture resembling that of conventional chewing gum It is also noted that even some variation may occur the main parameters remains broadly acceptable also while considering the associated release and the ability to provide a chewing gum which is reproducible.

Example 8

Evaluation of Nicotine Release from Nicotine Chewing Gum XIII of Example 2

The below table 8 illustrates API release (release of nicotine in the present example) of the chewing gum XIII of example 2 (corresponding to gum base III of example 1) and a chewing gum XX based on a standard gum baseX comprising natural resin, elastomer and no vinyl acetate-vinyl laurate copolymer.

The release of the API in this example is determined in vitro. The measurements were carried out according to the procedure set forth in the Ph. Eur. 6$^{th}$ ed. 2.9.25, in a phosphate buffer with pH=7.4, a chewing rate of 60 chew per minute, and with the temperature of the medium set at 37° C.

One piece of chewing gum was chewed at specified time intervals 0, 5, 10, 20 and 30 minutes. Then, the API content of the samples before and after chewing was analyzed according to standard HPLC-techniques.

Figure 3:
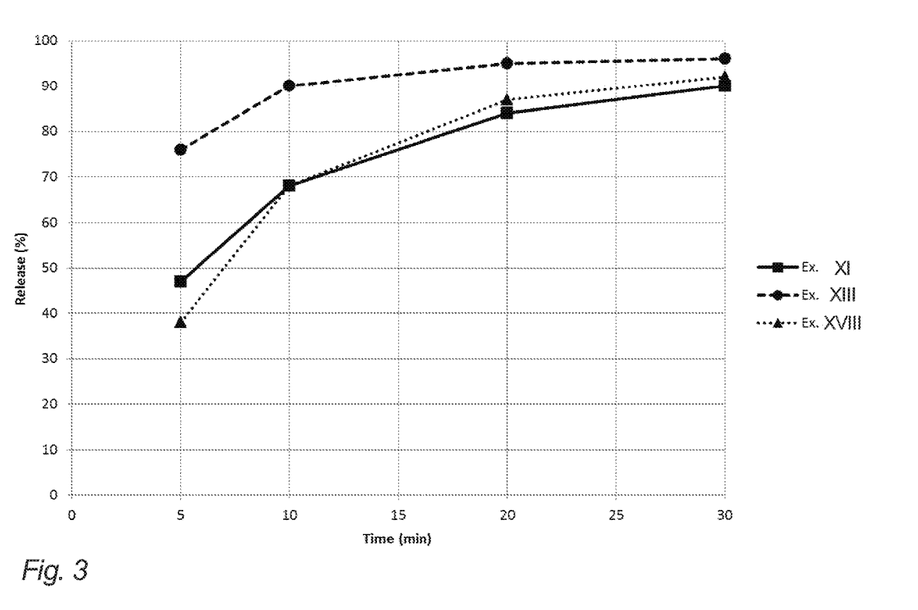
FIG. 3 illustrates the release of nicotine according to an example

It is noted that the chewing gum XIII demonstrates a high release of nicotine compared to example XI. This is also illustrated in FIG. 3.

TABLE 8

Nicotine release in percentage of actual content of nicotine contained in the chewing gum.

| Chewing gum according to example | % RELEASE at minutes | | | |
|---|---|---|---|---|
| | 5 min | 10 min | 20 min | 30 min |
| Ex. XI | 47 | 68 | 84 | 90 |
| Ex. XIII | 76 | 90 | 95 | 96 |

Example 9

Evaluation of Nicotine Release from Nicotine Chewing Gum XVIII of Example 2

The below table 9 illustrates API release (release of nicotine in the present example) of the chewing gum XVIII of example 2 (corresponding to gum base VIII of example 1) and a chewing gum XX based on a standard gum base XX comprising natural resin, elastomer and no vinyl acetate-vinyl laurate copolymer.

The release of the API in this example is determined in vitro. The measurements were carried out according to the procedure set forth in the Ph. Eur. 6$^{th}$ ed. 2.9.25, in a phosphate buffer with pH=7.4, a chewing rate of 60 chew per minute, and with the temperature of the medium set at 37° C.

One piece of chewing gum was chewed at specified time intervals 0, 5, 10, 20 and 30 minutes. Then, the API content of the samples before and after chewing was analyzed according to standard HPLC-techniques.

It is noted that the chewing gum XVIII demonstrates a lower initial release and subsequent comparable release compared to example XI. This is also illustrated in FIG. 3.

TABLE 9

Nicotine release in percentage of actual content of nicotine contained in the chewing gum.

| Chewing gum according to example | % RELEASE at minutes | | | |
|---|---|---|---|---|
| | 5 min | 10 min | 20 min | 30 min |
| Ex. XI | 47 | 68 | 84 | 90 |
| Ex. XVIII | 38 | 68 | 87 | 92 |

The invention claimed is:

1. A medical chewing gum comprising gum base components, chewing gum components, gum base polymers as part of the gum base components and nicotine,
    wherein the gum base polymers of the chewing gum are synthetic,
    the gum base polymers comprising a combined amount of polyvinyl acetate and vinyl laurate-vinyl acetate copolymer of more than 90% by weight of the gum base polymers,
    wherein the combined amount of polyvinyl acetate and vinyl laurate-vinyl acetate copolymer includes 20-95% by weight of polyvinyl acetate and 5-80% by weight of vinyl laurate-vinyl acetate copolymer, and
    wherein the chewing gum contains no polyterpene resins and no resins based on gum rosin, wood rosin or tall oil resin,
    whereby nicotine release is increased compared to a conventional nicotine chewing gum comprising natural resins having a similar level of burning.

2. The medical chewing gum according to claim 1, the medical chewing gum comprising gum base polymers, nicotine, and buffer,
    the gum base polymers comprising polyvinyl acetate and vinyl laurate-vinyl acetate copolymer in an amount of more than 90% by weight,
    wherein the gum base polymers include 20-95% by weight of polyvinyl acetate and 5-80% by weight of vinyl laurate-vinyl acetate copolymer, and
    wherein the chewing gum contains no polyterpene resins and no resins based on gum rosin, wood rosin or tall oil resin.

3. The medical chewing gum according to claim 2, wherein the buffer is present in an amount of 0.5 to 5% by weight of the chewing gum.

4. The medical chewing gum according to claim 1, wherein nicotine is present in an amount of 0.5-8 mg.

5. The medical chewing gum according to claim 1, wherein the weight ratio between polyvinyl acetate and vinyl laurate-vinyl acetate copolymer is from 8:1 to 2:3.

6. The medical chewing gum according to claim 1, wherein the weight ratio between vinyl acetate monomers of vinyl laurate-vinyl acetate copolymer and vinyl laurate monomers of vinyl laurate-vinyl acetate copolymer is less than 90:10.

7. The medical chewing gum according to claim 1, wherein the weight-average molecular weight Mw of polyvinyl acetate is from 5,000 to 120,000.

8. The medical chewing gum according to claim 1, wherein the gum base comprises 15-45% by weight of polyvinyl acetate, 10-30% by weight of vinyl laurate-vinyl acetate copolymers, 15-45% by weight of fillers, 5-30% by weight of waxes or fats, 1-10% by weight of plasticizers and 1-10% by weight of emulsifiers.

9. The medical chewing gum according to claim 1, wherein the gum base polymers further comprises one or more elastomers selected from the group consisting of styrene-butadiene copolymers (SBR), polyisobutylene, isobutylene-isoprene copolymers, polyethylene, polyurethane or any combination thereof.

10. The medical chewing gum according to claim 1, wherein the gum base polymers further comprises one or more elastomers in an amount of 0.1-10% by weight.

11. The medical chewing gum according to claim 1,
wherein the chewing gum comprises one or more fillers, and
wherein the filler is present in an amount of 5-45% by weight of the chewing gum.

12. The medical chewing gum according to claim 1, wherein the chewing gum comprises flavor in an amount between 0.01 and 10% by weight of the chewing gum.

13. The medical chewing gum according to claim 1, wherein the chewing gum comprises high intensity sweetener.

14. The medical chewing gum according to claim 1, wherein the chewing gum comprises bulk sweeteners including sugar and/or sugarless components.

15. The medical chewing gum according to claim 1, wherein the chewing gum comprises bulk sweetener in an amount of 5 to about 95% by weight of the chewing gum.

16. The medical chewing gum according to claim 1, wherein the chewing gum comprises gum base in an amount of 30-75% by weight of the chewing gum before any optionally applied coating.

17. The medical chewing gum according to claim 1, wherein the medical chewing gum has a tan (delta) of less than 1.2.

18. The chewing gum composition of claim 1, wherein the gum base polymers comprise 20-95% by weight of polyvinyl acetate.

19. The chewing gum composition of claim 1, wherein the gum base polymers comprise 5-80% by weight of vinyl laurate-vinyl acetate copolymer.

20. The medical chewing gum of claim 1, wherein the medical chewing gum comprises vinyl laurate-vinyl acetate copolymer in an amount of 38-40% by weight of the gum base polymers and polyvinyl acetate polymers in an amount of 60-62% by weight of the gum base.

21. A chewing gum comprising gum base polymers and nicotine,
wherein gum base polymers of the chewing gum are synthetic,
the gum base polymers comprising polyvinyl acetate and vinyl laurate-vinyl acetate copolymer in an amount of more than 90% by weight,
wherein the gum base polymers include 20-95% by weight of polyvinyl acetate and 5-80% by weight of vinyl laurate-vinyl acetate copolymer, and
wherein the chewing gum contains no polyterpene resins and no resins based on gum rosin, wood rosin or tall oil resin,
whereby nicotine release is increased compared to a conventional nicotine chewing gum comprising natural resins having a similar level of burning.

* * * * *